(12) United States Patent
Xia et al.

(10) Patent No.: US 9,594,104 B2
(45) Date of Patent: Mar. 14, 2017

(54) SIMULTANEOUS IMPEDANCE TESTING METHOD AND APPARATUS

(71) Applicant: Natus Medical Incorporated, San Carlos, CA (US)

(72) Inventors: Yongshou Xia, Ontario (CA); William Kolasa, Belleville, WI (US); Eric Garz, Lodi, WI (US)

(73) Assignee: Natus Medical Incorporated, San Carlos, CA (US)

( * ) Notice: Subject to any disclaimer, the term of this patent is extended or adjusted under 35 U.S.C. 154(b) by 84 days.

(21) Appl. No.: 14/521,382

(22) Filed: Oct. 22, 2014

(65) Prior Publication Data

US 2016/0116516 A1 Apr. 28, 2016

(51) Int. Cl.
  *A61B 5/04* (2006.01)
  *G01R 27/28* (2006.01)
  *G01R 27/00* (2006.01)

(52) U.S. Cl.
  CPC .......... *G01R 27/28* (2013.01); *G01R 27/00* (2013.01)

(58) Field of Classification Search
  CPC ....... A61B 5/0531; A61B 5/0476; A61B 5/04; A61B 5/0402; A61B 5/0478; A61B 5/053; A61B 5/0006; A61B 5/0488; A61B 5/0537; A61B 5/063; A61B 5/0809; A61B 5/7275; G01N 27/02

(Continued)

(56) References Cited

U.S. PATENT DOCUMENTS 5,020,541 A  6/1991  Marriott
5,921,939 A * 7/1999  Danielsson .......... A61B 5/0424
                                              600/509

(Continued)

FOREIGN PATENT DOCUMENTS

DE  19755418 A1  6/1999
EP   1512371 A1  9/2005

(Continued)

OTHER PUBLICATIONS

Yerworth, Rebecca J., et al; "Design and performance of the UCLH Mark 1b 64 channel electrical impedance tomography (EIT) system, optimized for imaging brain function."Physiological measurement 23, No. 1 (2002): 149.

(Continued)

*Primary Examiner* — Son Le
*Assistant Examiner* — Akm Zakaria
(74) *Attorney, Agent, or Firm* — Temmerman Law Office; Mathew J. Temmerman (57) ABSTRACT

A method and apparatus for determining the impedance of the plurality of channels comprising a plurality of channels having a plurality of first channels and a plurality of second channels, at least one reference channel, a signal generator electrically connected to the plurality of channels, a reference signal generator connected to the reference channel, at least one amplifier connected to each of the plurality of channels and the reference channel and at least one filter connected to an output of the at least one amplifier to filter the output signal from the at least one amplifier. The signal generator is configured to provide a plurality of input signals to the plurality of channels. The reference signal generator provides an input signal to the reference channel.

38 Claims, 5 Drawing Sheets

(58) Field of Classification Search
USPC .......................................................... 324/609
See application file for complete search history.

(56) References Cited

U.S. PATENT DOCUMENTS

| | | | |
|---|---|---|---|
| 6,516,218 | B1 | 2/2003 | Cheng et al. |
| 7,340,294 | B2 | 3/2008 | Gray |
| 8,068,905 | B2 | 11/2011 | Freeman et al. |
| 8,086,300 | B2 | 12/2011 | Herlerkson |
| 8,454,505 | B2 | 6/2013 | Yazleloglu et al. |
| 2003/0030426 | A1 | 2/2003 | Pickerd |
| 2003/0032989 | A1 | 2/2003 | Herleikson |
| 2005/0017781 | A1* | 1/2005 | Honda ................... H03K 5/151 327/295 |
| 2007/0038257 | A1* | 2/2007 | Gray ................... A61B 5/0424 607/8 |
| 2008/0269631 | A1 | 10/2008 | Denison |
| 2008/0303538 | A1 | 12/2008 | Orr |
| 2009/0133508 | A1 | 5/2009 | Johansson |
| 2010/0145217 | A1* | 6/2010 | Otto ..................... A61B 5/7225 600/544 |
| 2010/0225303 | A1 | 9/2010 | Min et al. |
| 2010/0321103 | A1* | 12/2010 | David ....................... G05F 3/08 327/551 |
| 2011/0066054 | A1* | 3/2011 | Yazicioglu ............... A61B 5/04 600/509 |
| 2011/0224528 | A1 | 9/2011 | Choi et al. |
| 2011/0301492 | A1* | 12/2011 | Lamp ................... A61B 5/0535 600/547 |
| 2012/0238855 | A1 | 9/2012 | Lanning et al. |
| 2012/0262186 | A1 | 10/2012 | Morrison et al. |
| 2014/0247058 | A1 | 9/2014 | Mortara |
| 2015/0036769 | A1* | 2/2015 | Peuscher ............ A61B 5/04004 375/319 |

FOREIGN PATENT DOCUMENTS

| | | |
|---|---|---|
| FR | 2908973 A1 | 11/2006 |
| JP | 2005080720 A | 3/2005 |
| KR | 2012005754 A | 1/2012 |
| WO | 2004075738 A3 | 9/2004 |
| WO | 2008063195 A1 | 5/2008 |
| WO | 2009023488 A1 | 2/2009 |

OTHER PUBLICATIONS

Praesomboon, Sukanya, et al; "Design and implementation of novel impedance measurement using digital sine-wave oscillator with optimum phase and amplitude." In ICCAS-SICE, 2009, pp. 5590-5595.IEEE, 2009.

* cited by examiner

SIMULTANEOUS IMPEDANCE TESTING METHOD AND APPARATUS

BACKGROUND OF THE DISCLOSURE

Technical Field of the Disclosure

The present embodiment relates in general to impedance testing methods. More specifically, the present disclosure relates to an apparatus and method that increases the speed in which the impedance of a plurality of electrodes can be measured.

Description of the Related Art

Biopotential measurements like electrocardiography (ECG), electromyography (EMG), and electroencephalography (EEG) measure heart, muscle, and brain activity (respectively) over time by measuring electric potentials on the surface of living tissue. Nervous stimuli and muscle contractions can be detected by measuring the ionic current flow in a patient. This is accomplished by using a plurality of biopotential electrodes. The fidelity of these measurements is limited by the effectiveness of the connection of the electrode to the patient. The resistance of the electrode system to the flow of electric currents, known as the electric impedance, characterizes the effectiveness of the connection. Typically, the lower the impedance, the higher the accuracy of the measurements. To ensure good signal quality, skin under the electrodes should preferably be prepared by abrasion. This process can be time-consuming especially when multiple electrodes are used. Adding to that, skin preparation may damage skin, which is undesirable particularly in long-term applications, as the presence of electrodes and electrolytic gel can cause irritation and risk of infection. Electrodes may also come into contact with blood products when skin is abraded. As a result, a risk of an infection with a blood-born pathogen exists.

The quality of the electrode contact is quantified by its electrical impedance. Electrode contact impedance is a relevant factor while considering the signal quality. Electrode contact impedance is expected to have a relationship to electrode contact noise, which consists of thermal noise generated at the resistive elements of the contact, metal-electrolyte noise and electrolyte-skin noise. Thermal noise generated at the electrode contact is proportional to the resistive part of the electrode contact impedance. However, total noise generated at the electrode contact is generally significantly larger than expected thermal noise. Hence to get a better signal quality for biopotential measurements the electrode contact impedance must be minimized by minimizing the total noise generated at the electrode contact.

It is often desirable to measure electrode impedances continuously in real time while the patient is being monitored. Biopotential measurements allow a user to measure electrode impedance in order to verify proper electrode application. One method to measure impedance involves injecting a sine wave current (typically 20 Hz) into an electrode and measuring the resulting amplitude, then calculating impedance. This measurement process requires a certain amount of time to complete. As the number of electrodes in use continues to increase (128→256→512 channels), the time required to cycle through and measure all electrodes becomes very long (minutes).

A solution to this is to measure multiple electrodes in parallel. All measurement currents flow back to the device through the ground electrode. Depending on the ground electrode impedance, a common mode (CM) voltage is generated by the measurements currents. The common mode rejection of the amplifier removes this CM voltage. However, as the number of parallel channels (and the current) is increased, the CM voltage continues to increase and eventually becomes an error in the electrode impedance measurements.

One existing apparatus and method for determining electrode impedances of a bioelectric signal-monitoring/recording system includes an amplifier and electrodes connected between a subject and the amplifier. An example apparatus includes: a voltage source outputting a voltage signal; a switching arrangement including an input electrically connected with the voltage source for receiving the voltage signal; an output electrically connected with the amplifier and the electrodes; switches between the input and the output; and a controller for opening and closing the switches to establish signal paths between the voltage source and the output. The controller calculates the electrode impedances relative to voltage outputs of the amplifier for each signal path. However, this apparatus and method do not reduce the common mode voltage across the electrode and can result in an error in the measurement of impedance as the number of electrodes is increased.

Another existing system discloses a wireless system for brain monitoring/mapping of patients with neurological-disorders. It includes a plurality of electrodes each configured for surface abutment of brain tissue and main circuitry for placement outside the patient's body configured to transmit power at radio frequencies and send and receive data using infrared energy. This system includes a remote circuitry having multiple analog switches configured to enable each electrode to be selected to deliver a selected amount of electrical current to the selected electrode. An analog switch integrated circuit is configured to select an electrode for delivery of stimulation current. However, in this embodiment, the measurement of impedance is done by selecting a pair of electrodes, one selected electrode and a reference electrode, to complete the circuit in which the impedance measurement is performed. Hence this method tends to take a significant amount of time to complete. In addition, by measuring the electrical impedance of multiple pairs of selected electrodes with a reference electrode, errors can occur in the measurement of impedance.

Another existing system discloses an apparatus and method that determines the quality of the connection of an electrode to a patient. The apparatus includes at least three electrodes selectively connected to a patient for sensing an electrophysiological signal representing a patient parameter. A current source is connected to each of at least three electrodes, and the current source is able to apply both a positive current and a negative current. A control processor is connected to the current source and the electrodes. The control processor identifies a number of unique electrode pairs and controls the current source to simultaneously apply a positive current to one electrode and a negative current to another electrode of each identified electrode pair to determine the connection quality. However, in this method, impedance for each electrode is calculated using the current and voltage differentials for each electrode pair and a connection quality for each electrode is determined by comparing the impedance for each electrode to a threshold impedance which gives an inaccurate value.

Therefore, there is a need for a method and an apparatus for measuring impedance of a plurality of electrodes that would minimize the errors in impedance measurement providing an accurate result. Such a method of measuring impedance would reduce the common mode voltage and provide an efficient means of measuring impedance in a reduced amount of time. Such a method would allow measuring the impedance of a plurality of channels with accuracy. Such a method would not damage the skin by the presence of electrode and electrolytic gel thereby reducing the possibly of contracting a skin infection. Finally, such a method and apparatus measures the plurality of electrode impedance simultaneously with reduced measurement time.

SUMMARY OF THE DISCLOSURE

To minimize the limitations found in the prior art, and to minimize other limitations that will be apparent upon the reading of this specification, the preferred embodiment of the present invention provides an apparatus and a method that increases the speed in which the impedance of a plurality of electrodes can be measured. The apparatus can be utilized in biopotential measurements involving a plurality of electrodes such as in electroencephalography (EEG), electromyography (EMG), electrocardiography (ECG), polysomnography (PSG) etc.

The apparatus comprises a plurality of channels having a plurality of first channels and a plurality of second channels, at least one reference channel, a signal generator electrically connected to the plurality of channels, a reference signal generator connected to the reference channel, at least one amplifier connected to each of the plurality of channels and the reference channel and at least one filter connected to an output of the at least one amplifier to filter the signal from the at least one amplifier. The signal generator is configured to provide a plurality of input signals to the plurality of channels. Each of the plurality of first channels is connected to the positive terminal of the at least one amplifier of the apparatus and supplied with a first input signal. Each of the plurality of second channels is connected to the positive terminal of the at least one amplifier and supplied with a second input signal. The first input signal and the second input signal are opposite in phase by connecting an inverter in parallel with the output of the signal generator. The reference signal generator provides an input signal to the negative terminal of the at least one amplifier through the reference channel. The plurality of channels, the reference and the patient ground (GND) are connected to the patient through a plurality of patient electrodes. As the first input signal, the second input signal and the input signal are applied to the plurality of channels and the reference channel, the common mode voltage across the plurality of channels is minimized.

The method for determining the impedance of the plurality of channels involves providing the apparatus for testing the impedance comprising the plurality of channels having the plurality of first channels and the plurality of second channels, at least one reference channel, the signal generator connected to the plurality of channels, the reference signal generator connected to the reference channel, at least one amplifier connected to each of the plurality of channels and the reference channel and at least one filter arrangement connected to an output of the at least one amplifier to filter the signal from the at least one amplifier. The method further involves (1) applying the first input signal to the plurality of first channels, (2) simultaneously applying the second input signal to the plurality of second channels such that the second input signal is opposite the phase of the first input signal, (3) simultaneously applying the input signal from the reference signal generator to the reference channel such that the frequency of the input signal is different from the frequency of the first input signal and the second input signal, and (4) measuring the output signal from the at least one filter arrangement and determining the impedance of the plurality of first channels, the plurality of second channels and the reference channel. The filter arrangement includes a first filter and a second filter utilized to filter a signal having different frequencies. Preferably, the first filter and the second filter can be a notch filter with different notch frequencies. In the simultaneous impedance testing method illustrated, the reference channel is configured as a reference potential with respect to the plurality of channels. The input signal, the first input signal and the second input signal can be selected from a group consisting of: a sinusoidal alternating current, an oscillating electric potential and a periodically varying voltage with high internal resistance. The input signal, the first input signal and the second input signal minimize the common mode voltage across the plurality of channels and the reference channel.

A first objective of the present invention is to provide an apparatus and a method that increases the speed in which the impedance of a plurality of electrodes can be measured.

A second objective of the present invention is to provide a method and an apparatus for measuring impedance of a plurality of channels that would minimize the errors in impedance measurement providing an accurate result.

A third objective of the present invention is to provide a method for measuring impedance that would reduce the common mode voltage and minimize the noise in the signal.

A fourth objective of the present invention is to provide a method and apparatus that are safe for a patient and do not cause damage to the skin by eliminating possible excessive current through the patient ground electrode during the high channel count configuration.

Another objective of the present invention is to provide a method and apparatus that provide an efficient means of measuring impedance in a reduced amount of time.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention Thus, the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features described herein may each be used independently of one another or in combination with other features. However, any single inventive feature may not address any of the problems discussed above or only address one of the problems discussed above. Further, one or more of the problems discussed above may not be fully addressed by any of the features described below.

In general, the present invention relates to an apparatus 100 and method that increases the speed of determining the impedance of a plurality of electrodes 102. The apparatus 100 for measuring contact impedance automatically measures, calculates and quantifies the quality of a connection between the electrode and a patient. The connection quality is determined by measuring impedance at the interface between an electrode connected to the patient and the skin of the patient. This is known as the contact impedance and the apparatus 100 advantageously measures and determines the contact impedance for each of the plurality of electrodes 102 during the course of patient monitoring.

Figure 1:
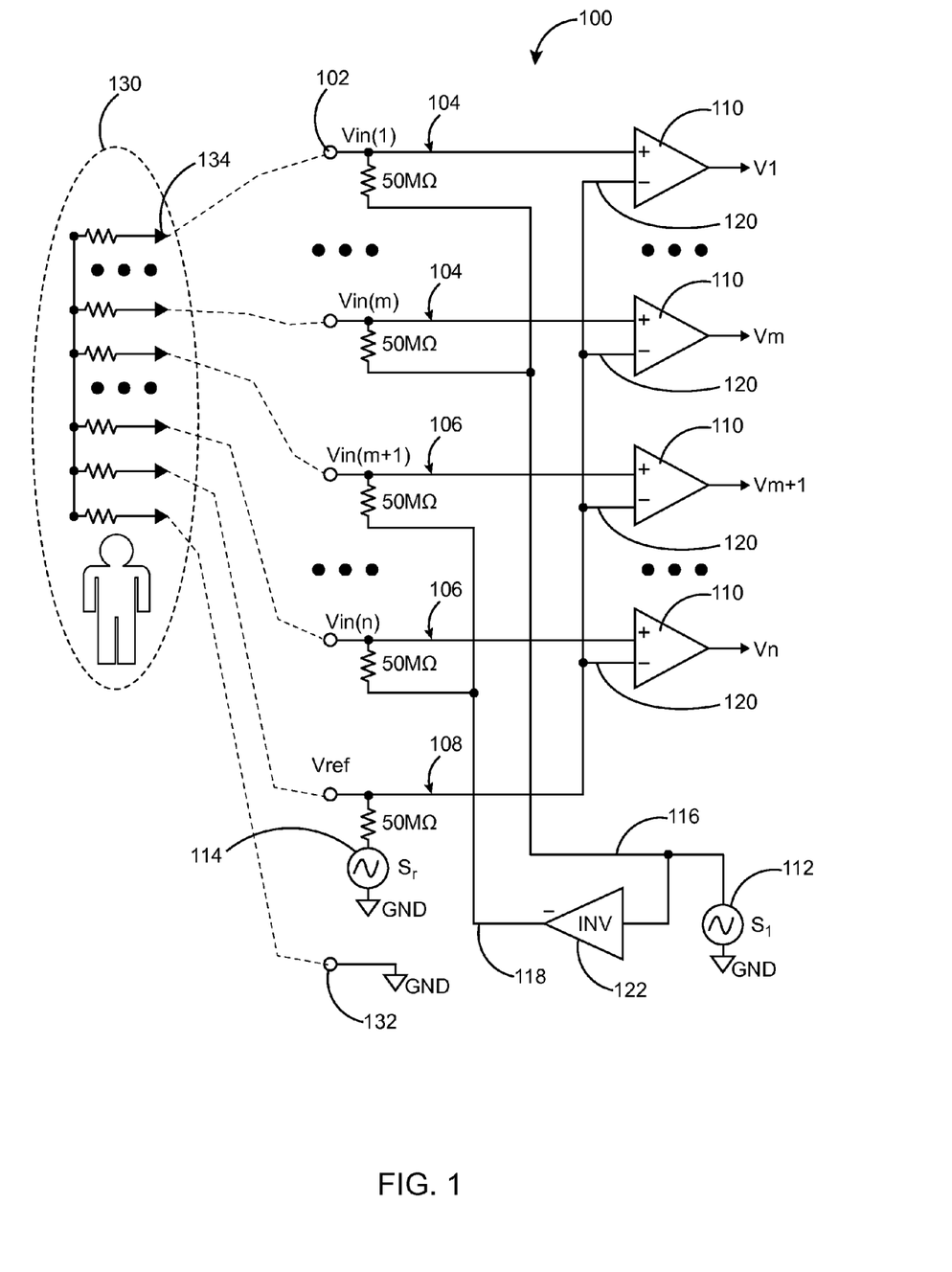
FIG. 1 is a schematic circuit diagram illustrating an impedance measurement apparatus for determining impedance of a plurality of channels according to the preferred embodiment of the present invention.

Referring to FIG. 1, a schematic circuit diagram illustrating an impedance measurement apparatus 100 for determining impedance of a plurality of channels 104, 106 and a patient impedance model 130 according to the preferred embodiment of the present invention is illustrated. The apparatus 100 can be utilized in biopotential measurements involving a plurality of electrodes 102 such as in electroencephalography (EEG), electromyography (EMG), electrocardiography (ECG), polysomnography (PSG) etc. The plurality of electrodes 102 is positioned over different positions of the patient impedance model 130 for performing various biopotential measurements. The apparatus 100 for determining impedance of a plurality of electrodes 102 comprises a plurality of channels 104, 106 having a plurality of first channels 104 and a plurality of second channels 106, at least one reference channel 108, a signal generator 112 electrically connected to the plurality of channels 104, 106, a reference signal generator 114 connected to the reference channel 108, at least one amplifier 110 connected to each of the plurality of channels 104, 106 and the reference channel 108 and at least one filter arrangement 124 (see FIG. 2) connected to the output of the at least one amplifier 110 to filter the output signal from the at least one amplifier 110. The signal generator 112 is configured to provide a plurality of input signals 116, 118 to the plurality of channels 104, 106. The plurality of first channels 104, for example, may include 1 . . . m channels and the plurality of second channels 106 may contain (m+1) n channels as illustrated in FIG. 1. Each of the plurality of first channels 104 is connected to the positive terminal of the at least one amplifier 110 and supplied with a first input signal 116. Each of the plurality of second channels 106 is connected to the positive terminal of the at least on amplifier 110 and supplied with a second input signal 118. The signal generator 112 provides the first input signal 116 and the second input signal 118 such that the first input signal 116 is opposite the phase with the second input signal 118. This is achieved by connecting an inverter 122 in parallel with the output of the signal generator 112 so that the first input signal 116 and the second input signal 118 are in opposite phase. A very low input potential, for example, Vin(1) . . . Vin(m) may be developed at the channels from 1 . . . m and Vin(m+1) . . . Vin(n) may be developed at the channels from m+1 . . . n and Vref for the reference channel 108. The at least one amplifier 110 can be a differential amplifier. The total noise generated at the electrode contact is generally significantly larger. The differential amplifier should have a common mode rejection factor sufficient to reduce unwanted differential output signals (as an equivalent differential input noise). The reference signal generator 114 is configured to provide an input signal 120 to the reference channel 108 such that the input signal 120 is orthogonal with respect to the first input signal 116 and the second input signal 118. The input signal 120 is applied to the negative terminal of the at least one amplifier 110 through the reference channel 108. The reference channel 108 is configured as a reference potential for the plurality of channels 104, 106. The plurality of channels 104, 106, the reference 108 and the patient ground (GND) 132 are connected to the patient through a plurality of patient electrodes 134. The first input signal 116, the second input signal 118 and the input signal 120 can be selected from a group consisting of: a sinusoidal alternating current, an oscillating electric potential and a periodically varying voltage with high internal resistance. The first input signal 116, the second input signal 118 and the input signal 120, for example, may be a symmetrical alternating current (AC) or a symmetrical direct current (DC). If it is not symmetrical, it at least has to be relatively symmetrical, such as DC levels centered around an arbitrary level instead of around a zero point or varying DC levels centered around an arbitrary level and not centered around a zero point. The corresponding amplified output voltages for example, can be V1 . . . Vm and Vm+1 . . . Vn.

As the first input signal 116, the second input signal 118 and the input signal 120 are applied to the plurality of channels 104, 106 and the reference channel 108, the common mode voltage across the plurality of channels 104, 106 is minimized. In one aspect of the present embodiment, the first input signal 116 is applied to the plurality of first channels 104 and the second input signal 118 opposite/inverse of the first input signal 116 is applied to the plurality of second channels 106. The input signal 120 having a different frequency with respect to the first input signal 116 and second input signal 118 is applied to the reference channel 108. The output from the at least one amplifier 110 contains an amplified signal from each of the plurality of channels 104, 106 and the reference channel 108. The amplified signal contains mixed frequencies of signals from the at least one of the plurality of channels 104, 106 and the reference channel 108. To separate the at least one channel frequency from the reference channel frequency, the output from the at least one amplifier 110 is given to a filter arrangement 124 as illustrated in FIG. 2.

Figure 3:
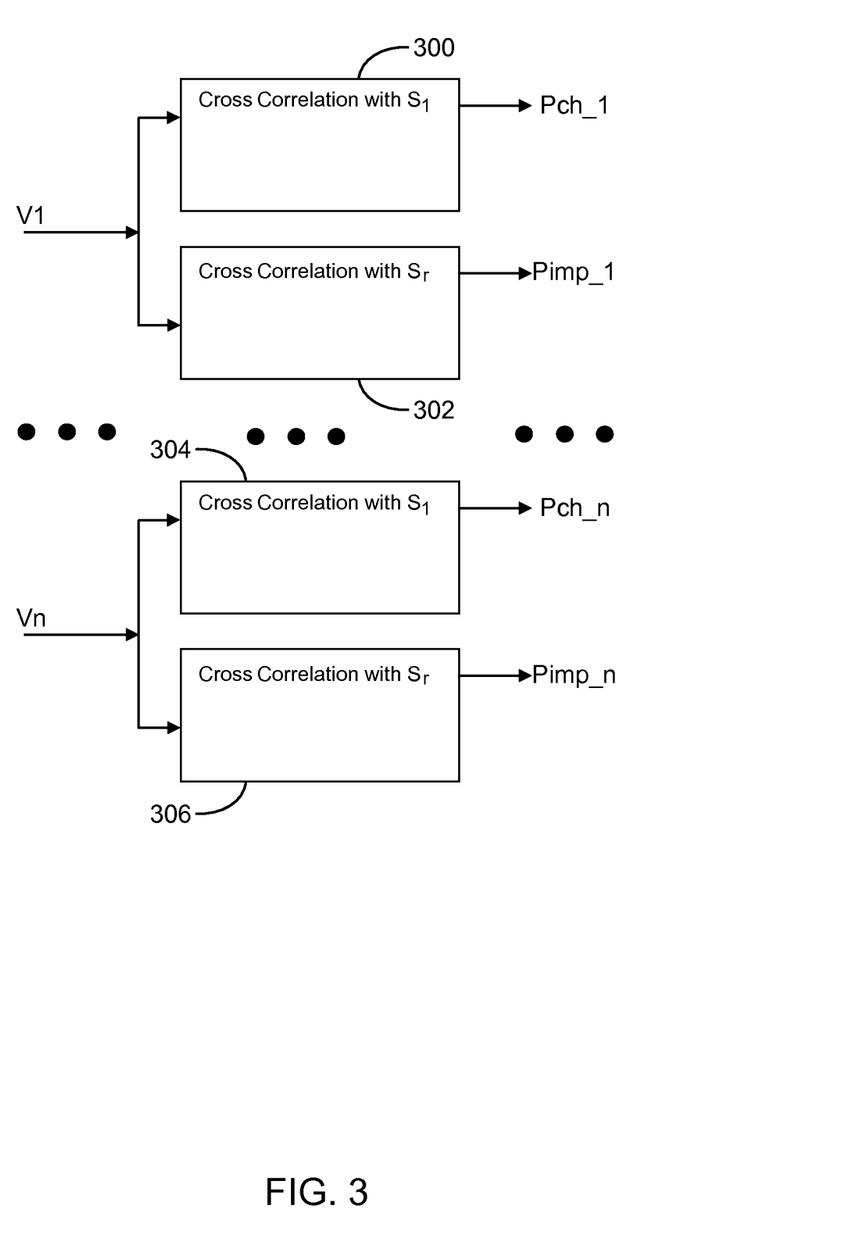
FIG. 3 illustrates a block diagram of the output obtained after performing a cross correlation procedure to determine the impedance of the plurality of channels according to the preferred embodiment of the present invention.

In another aspect of the present embodiment, the first input signal 116 is applied to the plurality of first channels 104 and the second input signal 118 opposite/inverse of the first input signal 116 is applied to the plurality of second channels 106. The input signal 120, having a phase shift with respect to the first input signal 116 and second input signal 118, is applied to the reference channel 108. The reference channel 108 is provided with the input signal 120 which has an orthogonal phase shift with respect to the first input signal 116 and the second input signal 118. The output from the at least one amplifier 110 contains an amplified signal from each of the plurality of channels 104, 106 and the reference channel 108. The amplified signal after multiple cycles of cross correlation operation with the first input signal 116 gives the cross correlated output signal corresponding to the first input signal 116 as illustrated in FIG. 3 from which the impedance can be calculated. Similarly, the impedance of each of the plurality of channels 104, 106 can be calculated.

Figure 2:
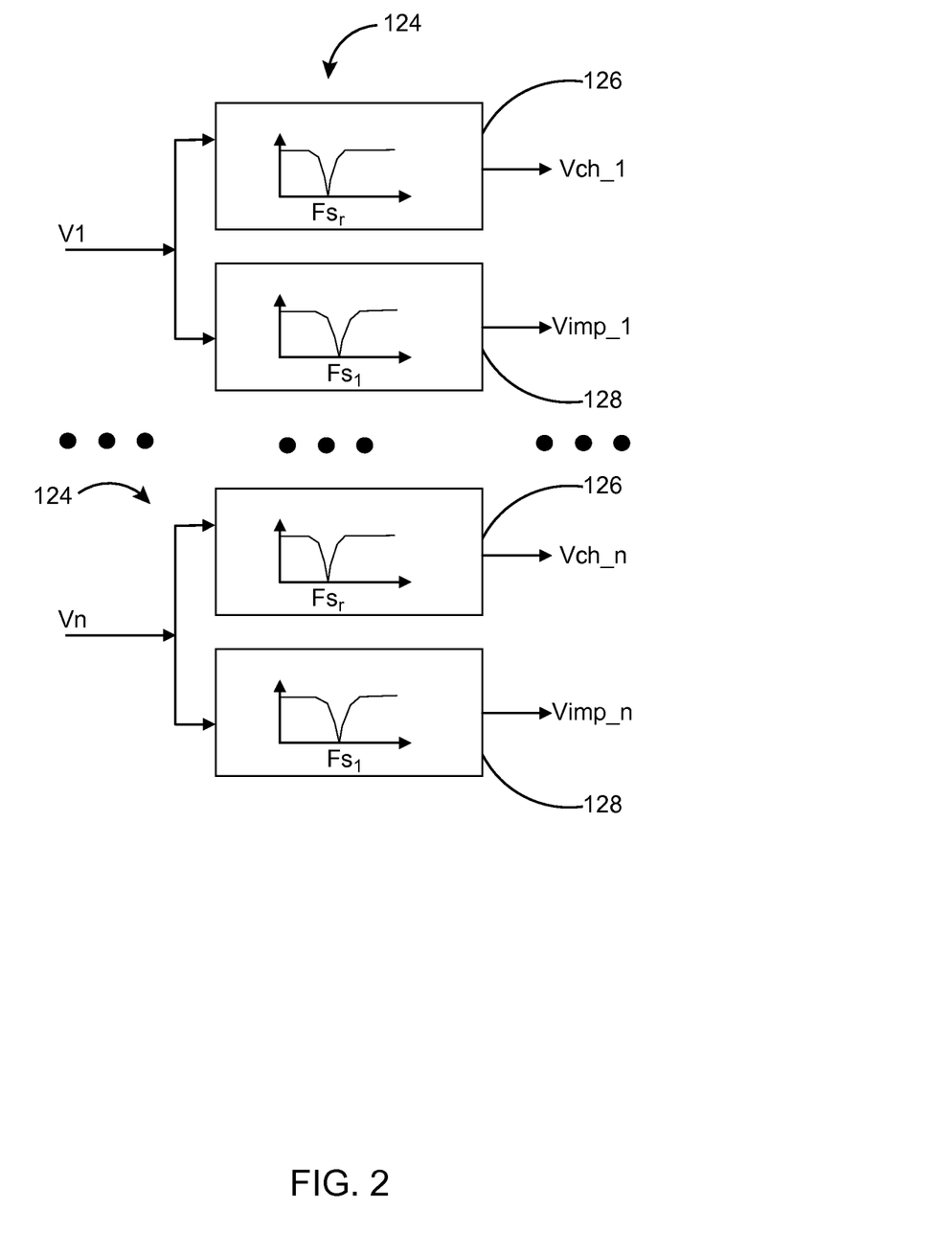
FIG. 2 illustrates a block diagram of a filter arrangement to determine the impedance of the plurality of channels according to the preferred embodiment of the present invention.

FIG. 2 illustrates a block diagram of a filter arrangement 124 to determine the impedance of the plurality of channels 104, 106 according to the preferred embodiment of the present invention. The filter arrangement 124 includes a first filter 126 and a second filter 128 utilized to filter a signal having different frequencies. Preferably, the first filter 126 and the second filter 128 can be a notch filter with different notch frequencies. The output from the at least one amplifier 110 is given to the filter arrangement 124. The first filter 126 may have a notch frequency the same as the input signal 120 given to the reference channel 108 thereby blocking the input signal frequency and providing an output signal having the frequency of the at least one of the plurality of channels 104, 106. The second filter 128 may have a notch frequency the same as the frequency of the at least one of the plurality of channels 104, 106 thereby blocking the frequency of the at least one of the plurality of channels 104, 106 and providing an output signal having the frequency of the input signal given to the reference channel 108.

Referring FIG. 2, for example, the plurality of first channels 104 may include 1 . . . m channels and the plurality of second channels 106 may contain (m+1) . . . n channels. The output from the at least one amplifier 110 for the first channel is V1. The V1 is passed through the filter arrangement 124. The first filter 126 may have a notch frequency the same as the input signal 120 given to the reference channel 108 thereby blocking the reference frequency and providing an output signal Vch_1 having the frequency of the first input signal 116 of the first channel. The second filter 128 may have a notch frequency the same as the frequency of the first input signal 116 of the first channel thereby blocking the first input signal frequency and providing an output signal Vimp_1 having the frequency of the input signal 120 given to the reference channel 108. In a similar way, for the $n^{th}$ channel, Vn is the input to the filter arrangement 124, which gives an output Vch_n having the signal frequency of the $n^{th}$ channel and Vimp_n having the frequency of the input signal 120 of the reference channel 108.

Therefore, in general the impedance for each of the plurality of channels 104, 106 can be calculated through the following formula:

$$IMP(j)=Kj*Vch\_j$$

$$IMP(ref)=Kr*Min(Vimp\_1, \ldots ,Vimp\_n)$$

where j=1, . . . , n; Kr, Kj are the calibration factors for each of the plurality of channels 104, 106 and Vch and Vimp are the root mean square value of the output from the filter arrangement 124.

FIG. 3 illustrates a block diagram of the output obtained after performing a cross correlation procedure to determine the impedance of the plurality of channels 104, 106 according to the preferred embodiment of the present invention. The first input signal 116 is applied to the plurality of first channels 104 and the second input signal 118 opposite of the first input signal 116 is applied to the plurality of second channels 106. The input signal 120, having a phase shift with respect to the first input signal 116 and second input signal 118, is applied to the reference channel 108. The reference channel 108 is provided with the input signal 120, which is orthogonal with respect to the first input signal 116 and the second input signal 118. The output from the at least one amplifier 110 contains an amplified signal from each of the plurality of channels 104, 106 and the reference channel 108. After multiple cycles of cross correlation operation with the first input signal 116, the uncorrelated signal is removed from the reference signal and gives the cross correlated output signal for each of the plurality of first channels 104 from which the impedance can be calculated.

For example, the output signal V1 from the at least one amplifier 110 of the $1^{st}$ channel undergoes multiple cycles of cross correlation operation with the first input signal 116 and gives the cross correlated output signal Pch_1 as illustrated by block 300. Also the cross correlation operation of V1 is performed with the input signal 120 of the reference channel 108 which gives the cross correlated output signal Pimp_1 as illustrated by block 302. In a similar way, for the $n^{th}$ channel, Vn undergoes multiple cycles of cross correlation operation and gives outputs Pch_n and Pimp_n as illustrated by block 304 and 306 respectively.

In general, the impedance of the plurality of channels 104, 106 can be calculated using the formula given below:

$$IMP(j)=Kj*\sqrt{Pch\_j}$$

$$IMP(ref)=Kr*\sqrt{Min(Pimp\_1,...,Pimp\_n)}$$

where j=1, . . . , n; Kr, Kj are the calibration factors for each of the plurality of channels 104, 106 and Pch and Pimp are calculated for multiple cycles of cross correlation wherein the cross correlation is defined by the equation:

$$Pch\_j = \sum_{m=0}^{\lambda} Vj[m]S1[m]$$

$$Pimp\_j = \sum_{m=0}^{\lambda} Vj[m]S1[m+\tau]$$

where $\lambda$ is the number of samples for multiple full cycles of S1, $\tau$ is the number of samples representing $\pi/2$ phase shift of the S1, S1[$m$] being the signal source for the plurality of inputs 116, 118 given to the plurality of channels 104, 106. Sr[m] being the signal source for the reference input 108. As an implementation, S1[$m$] and Sr[m] can be values from the sine wave lookup table which generates the impedance signal sources 112, 114.

Figure 4:
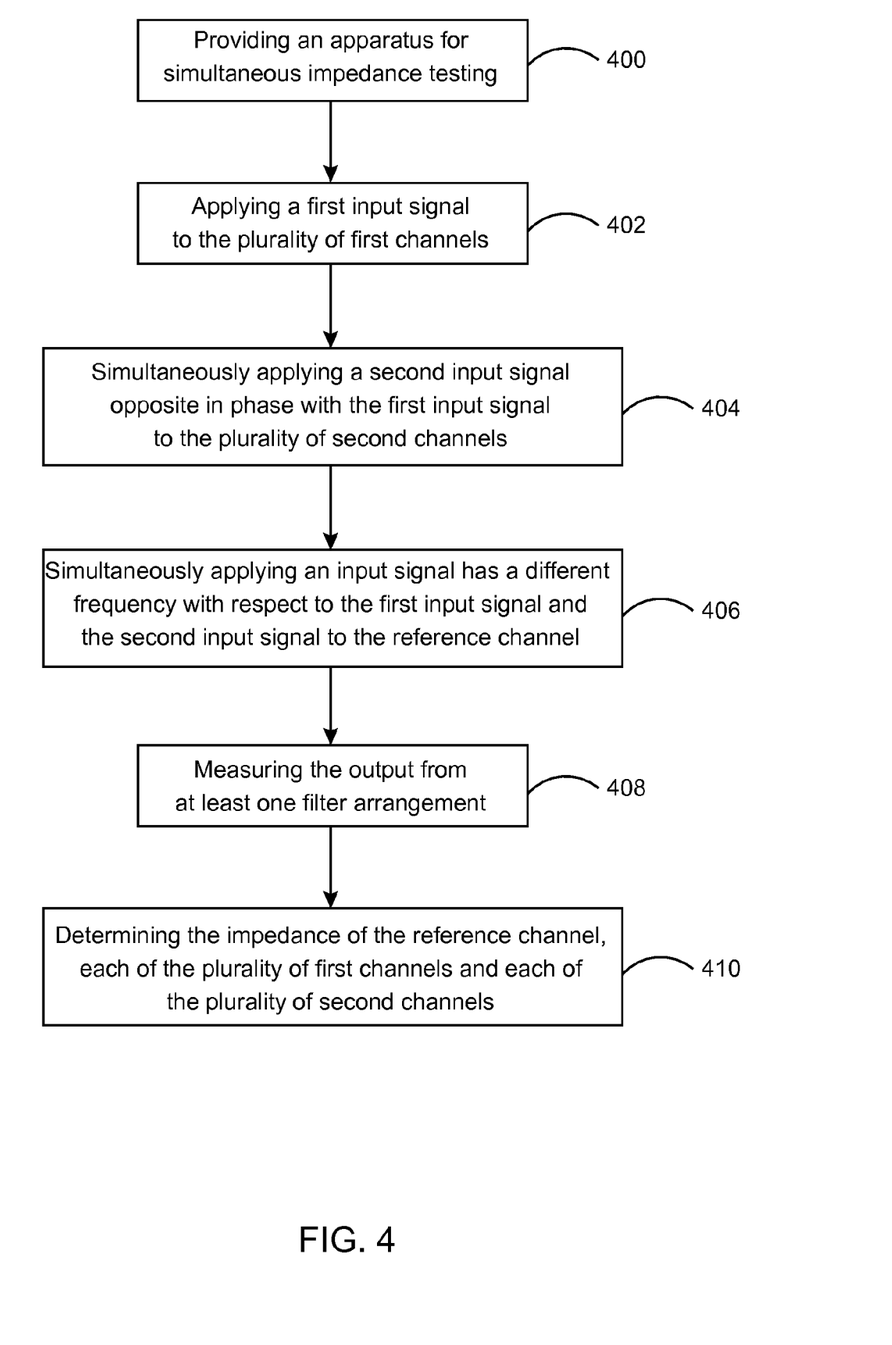
FIG. 4 illustrates a block diagram of a method for determining the impedance of the plurality of channels according to the preferred embodiment of the present invention.

FIG. 4 illustrates a block diagram of a method for determining the impedance of the plurality of channels 104, 106 according to the preferred embodiment of the present invention. In this preferred embodiment, the simultaneous impedance testing method of a plurality of electrodes 102 comprises the steps of: providing an apparatus 100 for testing the impedance comprising a plurality of channels 104, 106 having a plurality of first channels 104 and a plurality of second channels 106, at least one reference channel 108, a signal generator 112 connected to the plurality of channels 104, 106, a reference signal generator 108 connected to the reference channel 120, at least one amplifier 110 connected to each of the plurality of channels 104, 106 and the reference channel 108 and at least one filter 124 arrangement connected to an output of the at least one amplifier 110 to filter the signal from the at least one amplifier 110 as shown in block 400. Applying a first input signal 116 to the plurality of first channels 104 as indicated in block 402. Then, as indicated in block 404, simultaneously applying a second input signal 118 to the plurality of second channels 106 such that the second input signal 118 is opposite the phase of the first input signal 116. Simultaneously applying an input signal 120 from the reference signal generator 114 to the reference channel 108 such that the frequency of the input signal 120 is different from the frequency of the first input signal 116 and the second input signal 118 as shown in block 406. Then, measuring the output signal from the at least one filter arrangement 124 as indicated by block 408 and determining the impedance of the plurality of first channels 104, the plurality of second channels 106 and the reference channel 108 as indicated by block 410. The frequency of the input signal 120, the first input signal 116 and the second input signal 118 are different. In the simultaneous impedance testing method illustrated, the reference channel 108 is configured as a reference potential with respect to the plurality of channels 104, 106. The input signal 120, the first input signal 116 and the second input signal 118 can be selected from a group consisting of: a sinusoidal alternating current, an oscillating electric potential and a periodically varying voltage with high internal resistance. The input signal 120, the first input signal 116 and the second input signal 118 minimize the common mode voltage across the plurality of channels 104, 106 and the reference channel 108.

In one aspect of the present embodiment, the impedance of the plurality of channels 104, 106 is determined by applying the first input signal 116 to the plurality of first channels 104 and simultaneously applying the second input signal 118 inverse of the first input signal 116 to the plurality of second channels 106. Simultaneously determining the impedance of the reference channel 108 by applying the input signal 120 to the reference channel 108 such that the input signal 120 has an orthogonal phase shift with respect to the first input signal 116 and the second input signal 118.

In another aspect of the present embodiment, the impedance of the plurality of channels 104, 106 is determined by applying the input signal 120 to the reference channel 108 from the reference signal generator 114. Then, applying the first input signal 116 to the plurality of first channels 104 and simultaneously applying the second input signal 118 to the plurality of second channels 106 such that the second input signal 118 has an opposite phase with respect to the first input signal 116. The impedance of the reference channel 108 and the plurality of first channels 104 and the plurality of second channels 106 are determined from the cross correlation function.

In another aspect of the present embodiment, the impedance is determined by simultaneously applying a plurality of input signals 116, 118 to the plurality of channels 104, 106 such that the common mode voltage of the plurality of channels 104, 106 with respect to the reference channel 108 is minimized. Simultaneously, applying an input signal 120 to the reference channel 108 such that the input signal 120 has a different frequency with respect to the plurality of input signals 116, 118. Then, determining the impedance of the plurality of channels 104, 106 and the reference channel 108 by measuring the output from the at least one filter arrangement 124 connected therewith.

In another aspect of the present embodiment, the impedance is determined by simultaneously applying a plurality of input signals 116, 118 to the plurality of channels 104, 106 such that the common mode voltage of the plurality of channels 104, 106 with respect to the reference channel 108 is minimized. Simultaneously, applying an input signal 120 to the reference channel 108 such that the input signal 120 has a phase shift relative to the plurality of input signals 116, 118. Then, determining the impedance of the plurality of channels 104, 106 and the reference channel 108 by measuring the output after multiple cycles of cross correlation.

In yet another aspect of the present embodiment, the impedance is determined by applying an input signal 120 from the reference signal generator 114 to the reference channel 108. Then, by applying the first input signal 116 to the plurality of first channels 104 and simultaneously applying the second input signal 118 to the plurality of second channels 106 such that second input signal 118 has a phase opposite of the first input signal 116 and the frequency of the second input signal 118 is different from the frequency of the first input signal 116. By measuring the output from the at least one filter arrangement 124, the impedance of the reference channel 108, the plurality of first channels 104 and the plurality of second channels 106 can be determined.

Figure 5:
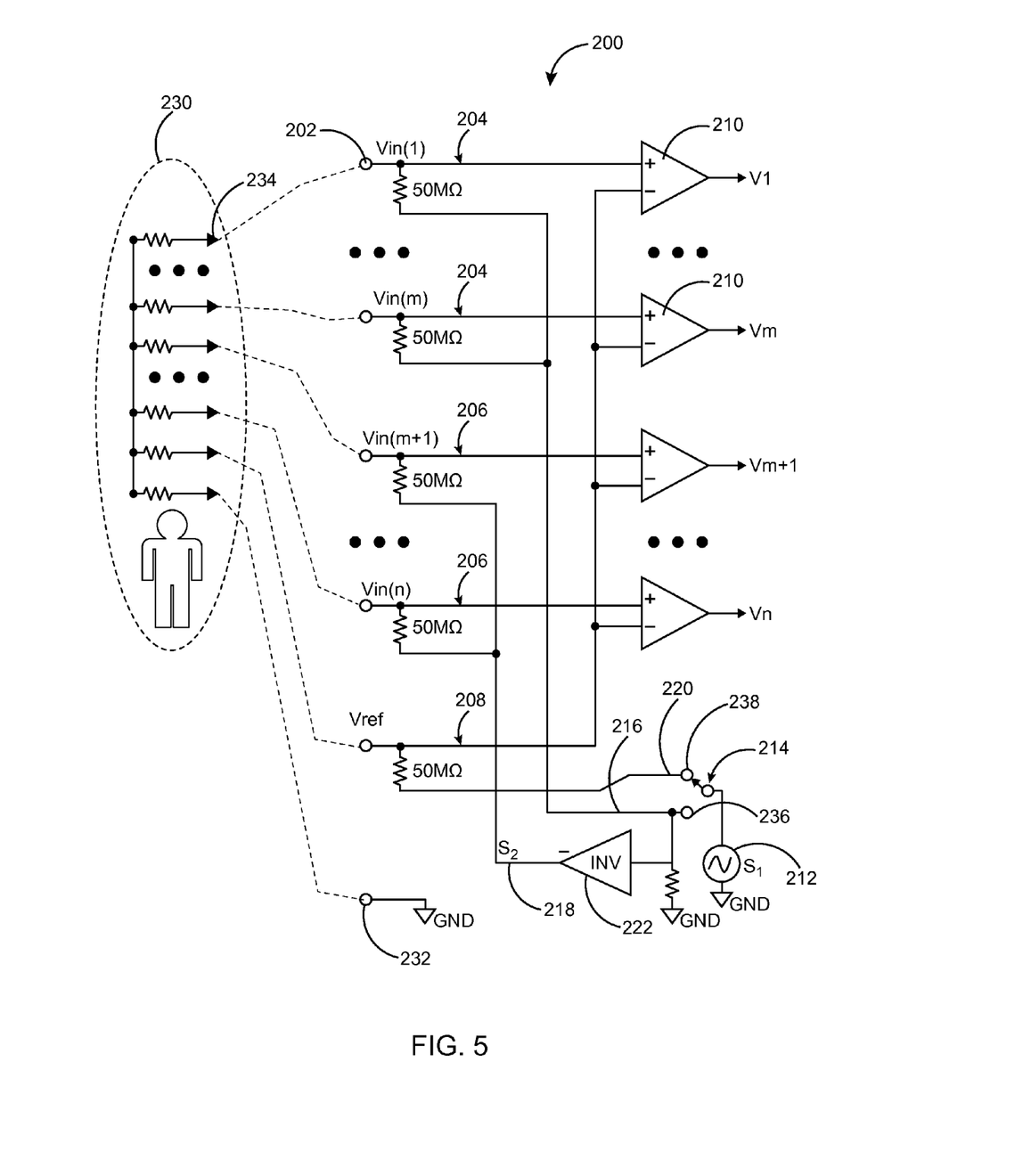
FIG. 5 is a schematic circuit diagram illustrating an impedance measurement apparatus for determining impedance of a plurality of channels according to one embodiment of the present invention.

FIG. 5 is a schematic circuit diagram illustrating an impedance measurement apparatus 200 for determining impedance of a plurality of channels 204, 206 according to one embodiment of the present invention. In this embodiment of the present invention, the apparatus 200 for determining impedance of a plurality of electrodes 202 comprises a plurality of channels 204, 206 having a plurality of first channels 204 and a plurality of second channels 206, at least one reference channel 208, a signal generator 212 electrically connected to the plurality of channels 204, 206 and the reference channel 208 by means of a switching arrangement 214, at least one amplifier 210 connected to each of the plurality of channels 204, 206 and the reference channel 208 and at least one filter 124 (see FIG. 2) connected to an output of the at least one amplifier 210 to filter the signal from the at least one amplifier 210. The plurality of electrodes 202 is attached to the plurality of patient electrodes 234 as illustrated by the patient impedance model 230. The signal generator 212 is configured to provide a plurality of input signals 216, 218 and 220 to the plurality of channels 204, 206 and the reference channel 208 by means of the switching arrangement 214. In one embodiment the switching arrangement 214 is a single pole double throw switch. The switching arrangement 214 has a first contact point 236 and a second contact point 238 as illustrated in FIG. 5. When the switching arrangement 214 is closed by sliding over the first contact point 236, the plurality of signals 216, 218 is applied to the plurality of channels 204, 206. When the switching arrangement 214 is closed by sliding over the second contact point 238, an input signal 220 is applied to the reference channel 208. The plurality of first channels 204, for example, may include from 1 to m channels and the plurality of second channels may contain (m+1) to n channels. Each of the plurality of first channels 204 and each of the plurality of second channels 206 is connected to the positive terminal of the at least one amplifier 210. When the switching arrangement 214 is at the first contact point 236, the signal generator 210 provides a first input signal 216 to the plurality of first channels 204 and a second input signal 218 to the plurality of second channels 206 such that the first input signal 216 is opposite the phase with the second input signal 218. This is achieved by connecting an inverter 222 connected in parallel after the first contact point 236 so that the first input signal 216 and the second input signal 218 are in opposite phase. The at least one amplifier 210 may be a differential amplifier comprising a common mode rejection factor sufficient to reduce unwanted differential output signals (as an equivalent differential input noise). When the switching arrangement 214 is at the second contact point 238, the input signal 220 is provided to the reference channel 208 such that the input signal 220 has a different frequency with respect to the first input signal 216 and the second input signal 218. The input signal 220 may be applied to the negative terminal of the at least one amplifier 210 connected through the reference channel 208. The reference channel 208 is configured as a reference potential for the plurality of channels 204, 206. The plurality of channels 204, 206, the reference 208 and the patient ground (GND) 232 are connected to the patient through the plurality of patient electrodes 234. The first input signal 216, the second input signal 218 and the input signal 220 may be selected from the group consisting of: a sinusoidal alternating current, an oscillating electric potential and a periodically varying voltage with high internal resistance. The first input signal 216, the second input signal 218 and the input signal 220, for example, may be a symmetrical alternating current (AC) or a symmetrical direct current (DC). If it is not symmetrical, it at least has to be the relatively symmetrical, such as DC levels centered around an arbitrary level instead of around a zero point or varying DC levels centered around an arbitrary level and not centered around a zero point.

When the switching arrangement 214 is at the first contact point 236, the impedance of the plurality of channels 204, 206 is determined by applying the plurality of input signals 216, 218 to the plurality of channels 204, 206 such that the common mode voltage of the plurality of channels 204, 206 with respect to the reference channel 208 is minimized. As a second step, when the switching arrangement 214 is at the second contact point 238, the impedance of the reference channel 208 is determined by applying an input signal 220 to the reference channel 208.

To determine the impedance of the plurality of channels 204, 206, the switching arrangement 214 is positioned at the first contact point 236. Then, by applying the plurality of input signals 216, 218 to the plurality of channels 204, 206 and measuring the amplified signal from the at least one amplifier 210 connected to each of the plurality of channels 204, 206. And calculating the impedance for each of the plurality of channels 204, 206. To determine the impedance of the reference channel 208, the switching arrangement 214 is positioned at the second contact point 238. Then, by applying the input signal 220 to the reference channel 208 and measuring the amplified signal from the at least one amplifier 210 connected to each of the plurality of channels 204, 206. And calculating the impedance of the reference channels 208. The amplified signal from each of the plurality of channels 204, 206 contains either signals from the reference channel 108 or signal from each of the plurality of channels 204, 206 depending on the switching arrangement 214 positions.

The impedances can be calculated through the following formula:
When the switching arrangement 214 is positioned at the first contact point 236, $$IMP(j)=Kj*Vch\_j$$

When the switching arrangement 214 is positioned at the second contact point 238, $$IMP(ref)=Kr*Min(Vch\_1, \ldots ,Vch\_n)$$

Where j=1, . . . , n; Kr, Kj are the calibration factors for each of the plurality of channels 204, 206. To improve the accuracy, Vch should be calculated for root mean square value from multiple full cycles.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

We claim:

1. An apparatus for determining impedance of a plurality of electrodes, comprising:
   a plurality of channels having a plurality of first channels and a plurality of second channels;
   at least one reference channel, the reference channel configured as a reference potential for the plurality of channels;
   a signal generator electrically connected to the plurality of channels, the signal generator configured to provide a plurality of input signals to the plurality of channels, the plurality of input signals includes a first input signal and a second input signal, the second input signal being opposite in phase of the first input signal and generated by means of an inverter connected in parallel with the output of the signal generator;
   a reference signal generator connected to the reference channel, the reference signal generator configured to provide an input signal to the reference channel;
   at least one amplifier connected to each of the plurality of channels and the reference channel to amplify the signal through the plurality of channels and the reference channel, each of the plurality of channels connected to a positive terminal of the amplifier and the reference channel connected to a negative terminal of the amplifier; and
   at least one filter arrangement having a first filter and a second filter, the at least one filter arrangement connected to an output of the at least one amplifier to filter the signal from the at least one amplifier;
   whereby the impedance of the plurality of channels can be determined from the output signal obtained from the at least one filter arrangement; and
   wherein the signal generator provides the plurality of inputs to the plurality of channels such that the common mode voltage imposed on the amplifier of each channel is minimized.

2. The apparatus for determining the impedance of claim 1 wherein the plurality of input signals and the input signal can be selected from a group consisting of: a sinusoidal alternating current, an oscillating electric potential and a periodically varying voltage with high internal resistance.

3. A simultaneous impedance testing method of a plurality of electrodes, the method comprising the steps of:
   a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;
   b) applying a first input signal to the plurality of first channels;

c) simultaneously applying a second input signal to the plurality of second channels such that the second input signal is opposite the phase of the first input signal;

d) simultaneously applying an input signal from the reference signal generator to the reference channel such that the frequency of the input signal is different from the frequency of the first input signal and the second input signal; and e) measuring the output signal from the at least one filter arrangement and determining the impedance of the plurality of first channels, the plurality of second channels and the reference channel;

f) wherein the input signal, the first input signal and the second input signal minimize the common mode voltage across the plurality of channels and the reference channel.

4. The simultaneous impedance testing method of claim 3 wherein the signal generator generates the first input signal and the second input signal.

5. The simultaneous impedance testing method of claim 3 wherein the second input signal is generated by means of an inverter connected to the output of the signal generator.

6. The simultaneous impedance testing method of claim 3 wherein the input signal, the first input signal and the second input signal can be selected from a group consisting of: a sinusoidal alternating current, an oscillating electric potential and a periodically varying voltage with high internal resistance.

7. The simultaneous impedance testing method of claim 3 wherein the reference channel is configured as a reference potential with respect to the plurality of channels.

8. The simultaneous impedance testing method of claim 3 wherein the frequency of the input signal, the first input signal and the second input signal are different.

9. A simultaneous impedance testing method, the method comprising the steps of:
a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;

b) determining the impedance of the plurality of channels by applying a first input signal to the plurality of first channels and simultaneously applying a second input signal inverse of the first input signal to the plurality of second channels; and c) simultaneously determining the impedance of the reference channel by applying an input signal to the reference channel such that the input signal has an orthogonal phase shift with respect to the first input signal and the second input signal;

d) wherein the phase shift in the input signal minimizes the common mode voltage across the plurality of channels.

10. The simultaneous impedance testing method of claim 9 wherein the second input signal applied to the plurality of second channels is inverse of the first input signal.

11. The simultaneous impedance testing method of claim 9 wherein the input signal, the first input signal and the second input signal can be selected from a group consisting of: a sinusoidal alternating current, an oscillating electric potential and a periodically varying voltage with high internal resistance.

12. The simultaneous impedance testing method of claim 9 wherein the signal generator generates the first input signal and the second input signal.

13. The simultaneous impedance testing method of claim 9 wherein the frequency of the input signal, the first input signal and the second input signal are the same.

14. The simultaneous impedance testing method of claim 9 wherein the frequency of the input signal, the first input signal and the second input signal are different.

15. An impedance testing method that minimizes the common mode voltage across a plurality of channels, the method comprising the steps of:
a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;

b) applying an input signal to the reference channel from the reference signal generator;

c) applying a first input signal to the plurality of first channels;

d) simultaneously applying a second input signal to the plurality of second channels such that the second input signal has the opposite phase of the first input signal;

e) determining the impedance of the reference channel by measuring the output from the filter arrangement connected to the reference channel; and f) determining the impedance of the plurality of first channels and the plurality of second channels by measuring the output from the at least one filter arrangement connected therewith;

g) wherein the input signal, the first input signal and the second input signal minimize the common mode voltage across the plurality of channels and the reference channel.

16. The impedance testing method of claim 15 wherein the frequency of the first input signal and the frequency of the second input signal are different.

17. The impedance testing method of claim 15 wherein the input signal, the first input signal and the second input signal can be selected from a group consisting of: a sinusoidal alternating current, an oscillating electric potential and a periodically varying voltage with high internal resistance.

18. The impedance testing method of claim 15 wherein the frequency of the input signal, the first input signal and the second input signal are different.

19. A simultaneous impedance testing method for a plurality of electrodes, the method comprising the steps of:
a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;

b) simultaneously applying a plurality of input signals to the plurality of channels such that the common mode voltage of the plurality of channels with respect to the reference channel is minimized;

c) simultaneously applying an input signal to the reference channel such that the input signal has a different frequency with respect to the plurality of input signals; and d) determining the impedance of the plurality of channels and the reference channel by measuring the output from the at least one filter arrangement connected therewith;

e) wherein the plurality of input signals applied to the plurality of channels minimizes the common mode voltage across the channels.

20. The simultaneous impedance testing method of claim 19 wherein the input signal and the plurality of input signals can be selected from a group consisting of: a sinusoidal alternating current, an oscillating electric potential and a periodically varying voltage with high internal resistance.

21. The simultaneous impedance testing method of claim 19 wherein the signal generator generates the plurality of input signals.

22. The simultaneous impedance testing method of claim 19 wherein the reference signal generator generates the input signal.

23. The simultaneous impedance testing method of claim 19 wherein the input signal and the plurality of input signals have the same frequency.

24. The simultaneous impedance testing method of claim 19 wherein the input signal and the plurality of input signals have at least two frequencies.

25. A simultaneous impedance testing method comprising the steps of:
a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;

b) determining the impedance of the plurality of channels by simultaneously applying a plurality of input signals to the plurality of channels such that the common mode voltage of the plurality of channels with respect to the reference channel is minimized and by measuring the output from the at least one filter arrangement connected therewith; and c) simultaneously determining the impedance of the reference channel by applying an input signal to the reference channel such that the input signal has a phase shift relative to the first input signal and measuring the output from the at least one filter arrangement connected therewith;

d) wherein the plurality of input signals is applied to the plurality of channels such that the common mode voltage of the plurality of channels with respect to the reference channel is minimized.

26. The simultaneous impedance testing method of claim 25 wherein the input signal and the plurality of input signals can be selected from a group consisting of: a sinusoidal alternating current, an oscillating electric potential and a periodically varying voltage with high internal resistance.

27. The simultaneous impedance testing method of claim 25 wherein the signal generator generates the plurality of input signals.

28. An impedance testing method involving a plurality of electrodes, the method comprising the steps of:
a) providing an apparatus for testing the impedance comprising a plurality of channels having a plurality of first channels and a plurality of second channels, at least one reference channel, a signal generator connected to the plurality of channels, a reference signal generator connected to the reference channel, at least one amplifier connected to each of the plurality of channels and the reference channel and at least one filter arrangement connected to an output of the at least one amplifier to filter the signal from the at least one amplifier;

b) applying an input signal from the reference signal generator to the reference channel;

c) applying a first input signal to the plurality of first channels;

d) simultaneously applying a second input signal to the plurality of second channels such that second input signal has a phase opposite of the first input signal and the frequency of the second input signal is different from the frequency of the first input signal;

e) measuring the output from the at least one filter arrangement and determining the impedance of the reference channel; and f) measuring the output from the at least one filter arrangement connected therewith and determining the impedance of the plurality of first channels and the plurality of second channels;

g) wherein the input signal, the first input signal and the second input signal minimize the common mode voltage across the plurality of channels and the reference channel.

29. The impedance testing method of claim 28 wherein the input signal, the first input signal and the second input signal can be selected from a group consisting of: a sinusoidal alternating current, an oscillating electric potential and a periodically varying voltage with high internal resistance.

30. The impedance testing method of claim 28 wherein the signal generator generates the first input signal and the second input signal.

31. The simultaneous impedance testing method of claim 28 wherein the first input signal is applied to the plurality of channels such that the common mode voltage of the plurality of channels with respect to the reference channel is minimized.

32. A simultaneous impedance testing method of a plurality of electrodes, the method comprising the steps of:
a) providing an apparatus for testing the impedance of the plurality of electrodes comprising a plurality of channels having a plurality of first channels and a plurality of second channels, at least one reference channel, a signal generator connected to the plurality of channels and the reference by means of a switching arrangement, at least one amplifier connected to each of the plurality of channels and the reference channel;

b) applying a plurality of input signals to the plurality of channels by means of the switching arrangement;

c) simultaneously measuring the output from the at least one amplifier connected to each of the plurality of channels and determining the impedance of the plurality of channels;

d) applying an input signal to the reference channel by means of the switching arrangement; and e) simultaneously measuring the output from the at least one amplifier connected to each of the plurality of channels and determining the impedance of the reference channel;

f) wherein the input signal, the first input signal and the second input signal minimize the common mode voltage across the plurality of channels and the reference channel.

33. The simultaneous impedance testing method of claim 32 wherein the signal generator generates the plurality of input signals and the input signal.

34. The simultaneous impedance testing method of claim 32 wherein the switching arrangement has a first contact point and a second contact point.

35. The simultaneous impedance testing method of claim 34 wherein the plurality of input signals is given to the plurality of channels when the switching arrangement is at the first contact point.

36. The simultaneous impedance testing method of claim 34 wherein the input signal is given to the reference channel when the switching arrangement is at the second contact point.

37. The simultaneous impedance testing method of claim 32 wherein a first input signal is given to the plurality of first channels and a second input signal is given to the plurality of second channels by means of an inverter connected in parallel with the first contact point of the switching arrangement.

38. The simultaneous impedance testing method of claim 32 wherein the input signal, the first input signal and the second input signal can be selected from a group consisting of: a sinusoidal alternating current, an oscillating electric potential and a periodically varying voltage with high internal resistance.

* * * * *